United States Patent [19]

Rinehart

[11] Patent Number: 5,735,895
[45] Date of Patent: Apr. 7, 1998

[54] ARTIFICIAL ANIMAL EYE WITH NICTITATING MEMBRANE

[75] Inventor: John R. Rinehart, Milton, Wis.

[73] Assignee: Rinehart Family Company, Janesville, Wis.

[21] Appl. No.: 761,643

[22] Filed: Dec. 6, 1996

[51] Int. Cl.⁶ ..................................................... A61F 2/14
[52] U.S. Cl. .................. 623/4; 446/389; 446/392
[58] Field of Search .............. 623/4; 446/341–348, 446/389–392

[56] References Cited

U.S. PATENT DOCUMENTS

| | | | |
|---|---|---|---|
| 2,497,872 | 2/1950 | Erpf et al. | 623/4 |
| 2,653,328 | 9/1953 | Anderson et al. | 623/4 |
| 3,846,199 | 11/1974 | Cappilli | 623/4 X |
| 4,432,919 | 2/1984 | Rinehart . | |
| 4,477,500 | 10/1984 | Powell | 428/16 |
| 4,511,522 | 4/1985 | Rinehart . | |
| 4,515,340 | 5/1985 | Rinehart . | |
| 4,596,683 | 6/1986 | Powell . | |
| 4,642,209 | 2/1987 | Powell . | |
| 4,753,412 | 6/1988 | Johnson . | |
| 4,822,397 | 4/1989 | Crossley | 65/107 |
| 5,540,612 | 7/1996 | Mendez | 446/392 |

*Primary Examiner*—Mary Beth Jones
*Attorney, Agent, or Firm*—Foley & Lardner

[57] ABSTRACT

An artificial animal eye for use in taxidermy and including a nictitating membrane integrally formed thereon is provided. The artificial animal eye is formed on a transparent eyepiece blank, such as a clear glass eyepiece, having a concave inner surface and a convex outer surface. Animal eye coloration is applied to the concave inner surface of the eyepiece. The integrally formed nictitating membrane is formed as a dark coloration applied along a portion of the circumferential edge of the convex outer surface of the eyepiece. The nictitating membrane coloration may be formed using a leaded glass enamel glaze mixture which is applied to the outer surface of the eyepiece in the shape of the nictitating membrane. Firing the eyepiece causes the glaze to fuse with the eyepiece glass, integrally forming the nictitating membrane on the eyepiece. For artificial deer eyes, the nictitating membrane is crescent shaped, having a wide central portion aligned with the long (horizontal) axis of an elongated eyepiece pupil, with the ends of the nictitating membrane crescent shape terminating at points on the circumferential edge of the eyepiece on opposite sides of the pupil and aligned with the short (vertical) axis of the eyepiece pupil.

5 Claims, 4 Drawing Sheets

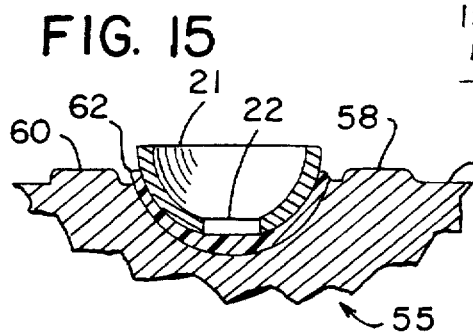
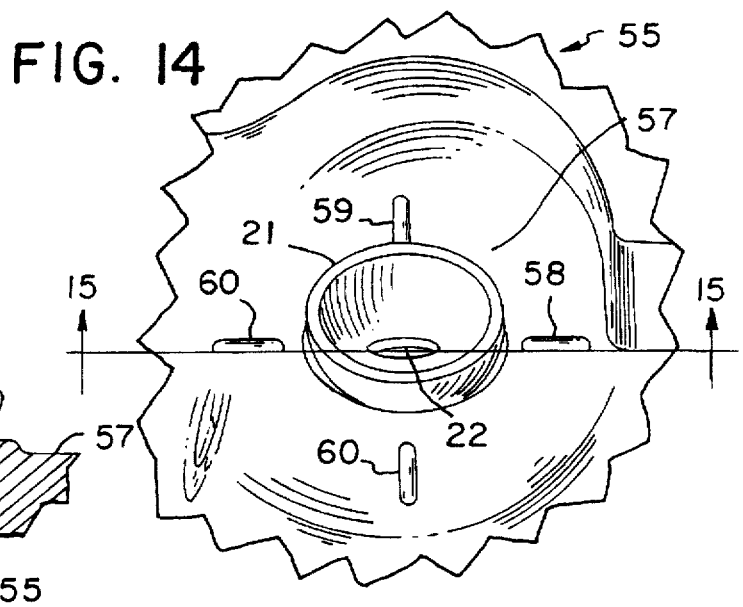
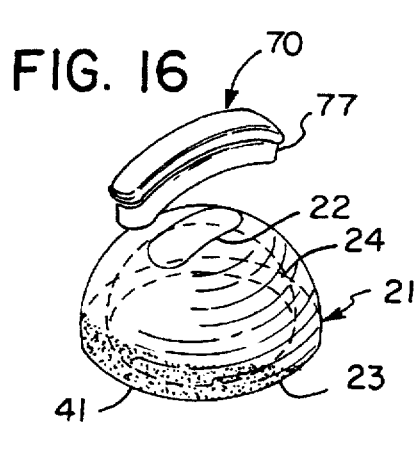
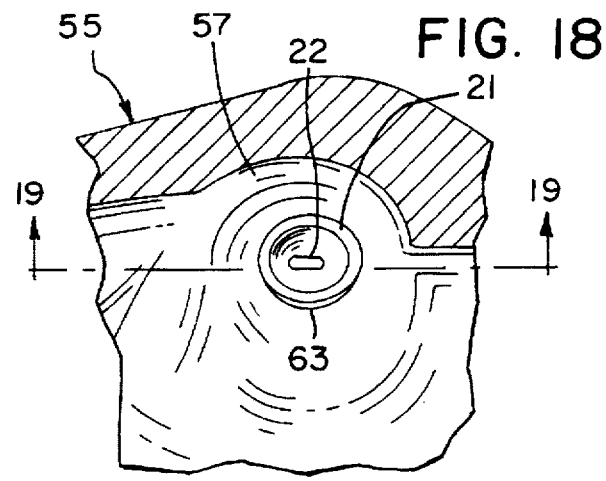
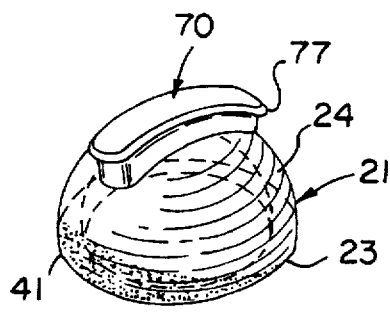
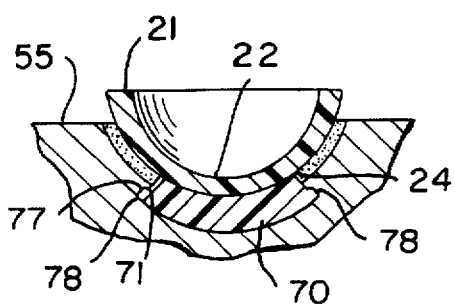

ARTIFICIAL ANIMAL EYE WITH NICTITATING MEMBRANE

FIELD OF THE INVENTION

This invention pertains generally to the field of taxidermy, and more particularly to artificial animal eyes used in the art of taxidermy.

BACKGROUND OF THE INVENTION

Taxidermists mount animal head skins over molded animal head mannikins, such as deer head mannikins, and secure the result to a wall plaque or the like for use as a trophy. These molded mannikins, usually of lightweight polyurethane foam material, have very large eye socket cavities into each of which the taxidermist must mount an artificial animal eye. The process of mounting the animal eye in the mannikin typically also involves making and mounting eye-surrounding anatomy contour features, usually of modeling clay, and, if the eye is of the elongated pupil type, such as with a deer, rotating the eye to a proper orientation for correct and natural appearance.

An artificial animal eye used in taxidermy is typically made from a transparent glass or plastic eyepiece blank having a concave inner surface and a convex outer surface. Coloration is applied to the concave inner surface of the eyepiece to realistically match the natural color of the animal's eye. For glass eyepieces, natural eye coloration is typically accomplished using variously colored glazes which are applied to the concave inner surface of the eyepiece and fused to the eyepiece by firing in a kiln.

A nictitating membrane is a thin membrane found in many animals, including deer, at the inner angle or beneath the lower lid of the eye, and capable of extending across the eyeball. To enhance the realism of a mounted animal head skin, it is preferable that the artificial eye, such as an artificial deer eye, include a feature corresponding to the nictitating membrane found in the live animal. Nictitating membrane features for artificial deer eyes have previously been implemented using thin black strips, usually of plastic, in the crescent shape of a nictitating membrane. The nictitating membrane piece is mounted by the taxidermist, along with the artificial deer eye itself, into the animal head mannikin. The positioning and securing of the artificial eye and the nictitating membrane piece in the correct anatomical position in the animal head mannikin demands considerable time and skill of the taxidermist.

U.S. Pat. Nos. 4,432,919, 4,511,522, and 4,515,340, issued to John R. Rinehart, disclose molds and molding methods for producing taxidermy animal head mannikins complete with eyes and eye-surrounding anatomy as part of the mannikin when it comes out of the mold. Thus, the taxidermist need not spend time and skill positioning or mounting the eyes, or filling in and contouring around the eyes to form correct anatomical eye-surrounding features. The mannikin molds disclosed in these patents also include reference indicia in the cavity surfaces of the mold near the edge of eye socket recesses. These reference indicia are used to align the artificial eyepiece that is inserted in the eye socket recess into the correct anatomical orientation. The taxidermy mannikin is formed by filing the mold with a polyurethane foam material which surrounds an exposed back portion of the artificial eyepiece, securing it therein. These patents also disclose the use of a removable (cleanable) adhesive to hold the eyepiece in the correct position on the mold during the molding operation. The adhesive is removable (cleanable) from the outer surface of the eyepiece after the molding operation is complete, and the completed mannikin is removed from the mold. Other methods of placing and securing an eyepiece in correct anatomical position in an animal head mannikin mold are disclosed in U.S. Pat. Nos. 4,596,683, to Powell (disclosing an eyepiece having a circular flange with two notches which mate with two diametrically opposed lugs on edges of the mold eye socket recess to lock the eyepiece into position), 4,642,209, also to Powell (disclosing a method of holding an eyepiece in position on the mold during the molding process by applying an adhesive onto the mold eye socket which selectively releases from the eye but remains adhered to the mold when the parts of the mold are separated to remove the completely formed mannikin), and 4,753,412, to Johnson (disclosing a method for locating an eyepiece in correct anatomical position in the mannikin mold using a locator piece, attached to the front of the eyepiece with a removable adhesive, that is positioned in a corresponding locator socket in the mold eye socket).

SUMMARY OF THE INVENTION

The present invention provides an artificial animal eye, such as an artificial deer eye for use in taxidermy, having a realistic nictitating membrane feature integrally formed on the outer surface thereof. Since the nictitating membrane is integrally formed on the artificial eyepiece, the taxidermist need only accurately position the artificial eyepiece itself in a taxidermy mannikin to achieve a realistic mount. The taxidermist thus need not expend additional time and effort positioning a separate nictitating membrane piece in the taxidermy mannikin, and need not be concerned that the separate nictitating membrane piece is placed in a proper anatomical position with respect to the artificial eye. An artificial eye with a nictitating membrane integrally formed thereon in accordance with the present invention may be employed in taxidermy mannikins formed using molding methods for producing mannikins complete with eyes including nictitating membranes fixed in proper anatomical position thereon along with eye-surrounding anatomical features.

The present invention provides a method for producing a realistic appearing artificial animal eye with a nictitating membrane integrally formed on the outer surface thereof. The nictitating membrane may be formed on a transparent eyepiece blank, such as of glass, that is colored on the concave inner surface thereof to realistically match the natural color of an animal's eye. Natural coloration of glass eyepiece blanks may be achieved through the application of colored glazes to selected areas on the concave inner surface of the eyepiece blank, followed by firing of the eyepiece to fuse the glazes with the glass. Conventional low-fire leaded or non-leaded glass enamel glazes may be used to achieve natural eye coloration and texture. An eyepiece template and various application methods, including air brushing, may be used to apply the different colors and textures to the selected areas on the concave inner surface of the eyepiece. Alternatively, an integrally formed nictitating membrane in accordance with the present invention may be formed on the outer surface of an eyepiece having natural eye coloration already formed on the concave inner surface thereof.

An integrally formed nictitating membrane in accordance with the present invention is formed by fusing coloration in the shape of the membrane unto the outer convex surface of the eyepiece. This may be accomplished by applying a colored glaze onto the convex outer surface of the glass eyepiece blank. The glaze is preferably a low-fire leaded glass enamel glaze, including a glaze powder mixed with distilled water, alcohol, and shellac. A brush dipped in the glaze mixture may be used to apply the glaze to the concave outer surface of the glass eyepiece in the shape of the nictitating membrane. For an artificial deer eye, for example, the nictitating membrane is crescent shaped, and is applied to the convex outer surface of the eyepiece along a portion of the edge thereof. Using a brush, and starting at a point on the edge of the eyepiece aligned with the short (vertical) axis of the elongated deer eye pupil, the glaze is flowed onto the outer surface of the eyepiece, along the outer edge thereof, in one stroke to a point on the edge of the eyepiece opposite the starting point. The glaze is thereby applied in a crescent shape, with the widest point of the crescent extending onto the outer surface of the eyepiece at a point midway between the ends of the crescent and aligned with the long (horizontal) axis of the elongated deer eye pupil. For an artificial deer eye, the widest portion of the nictitating membrane crescent will extend approximately one-quarter of an inch from the edge of the artificial eyepiece onto the concave outer surface of the eyepiece. After the glaze is allowed to dry, the artificial eyepiece is fired in a kiln. During firing, the colored glaze forming the nictitating membrane actually fuses with the glass of the eyepiece, becoming an integrally formed part of the artificial animal eye.

An artificial animal eye with integrally formed nictitating membrane in accordance with the present invention may be insert molded into an animal head mannikin. The taxidermy mannikin is made using a mold which includes a pair of mold half-parts. Each half of the mold has a cavity surface contoured for correct anatomical formation of the features of half of the mannikin, and includes an eye socket recess in the cavity surface shaped for snugly receiving the front portion of the artificial eye while leaving the rear portion of the eyepiece projecting into the mold cavity. The mold cavity may include reference indicia near the edge of the eye socket recess, which may be used as an aid in aligning the eyepiece in the proper anatomical orientation in the socket. Alternatively, proper anatomical orientation of the eyepiece may be achieved using a locator socket positioned in the eye socket recess and designed to receive a mating locator piece which is affixed to the outer surface of the eyepiece using a removable (cleanable) adhesive. In either case, the eyepiece may be secured in position in the mold during the molding operation using a similar removable (cleanable) adhesive.

With the eyepiece placed in the mold and oriented correctly, the mold is closed. A polyurethane foam material is then injected into the mold to form the animal head mannikin. After the foam hardens, the animal head mannikin is removed from the mold, with the artificial eyepiece, including an integrally formed nictitating membrane, properly positioned in correct anatomical position thereon.

An artificial animal eye having a realistic nictitating membrane integrally formed thereon in accordance with the present invention allows a taxidermist to more rapidly and accurately create a realistic taxidermy mount. The position of the nictitating membrane with respect to the other features of the artificial eye, such as the pupil, is accurately established during fabrication of the artificial eye. Thus, the taxidermist need only be concerned with positioning one piece, the artificial eye with nictitating membrane integrally formed thereon, in the animal head mannikin. An artificial animal eye with integrally formed nictitating membrane may also be insert molded in proper anatomical position in an animal head mannikin, thus further facilitating rapid and accurate creation of a realistic taxidermy mount.

BRIEF DESCRIPTION OF THE DRAWINGS

FIG. 14 is an enlarged view of a portion of the mold shown in FIG. 13, showing an artificial eyepiece in accordance with the present invention inserted therein in proper anatomical orientation.

FIG. 15 is a section view taken along line 15—15 of FIG. 14.

FIG. 16 is a perspective view of an eyepiece with integrally formed nictitating membrane in accordance with the present invention and an elongated mating key projecting away from the eyepiece.

FIG. 17 is a perspective view of the eyepiece of FIG. 16 with the elongated mating key affixed thereto.

FIG. 18 is an enlarged view of a portion of a taxidermy mold showing the eyepiece of FIG. 17 inserted therein in proper anatomical orientation.

FIG. 19 is a section view taken along section line 19—19 of FIG. 18.

DETAILED DESCRIPTION OF THE INVENTION

Figure 1:
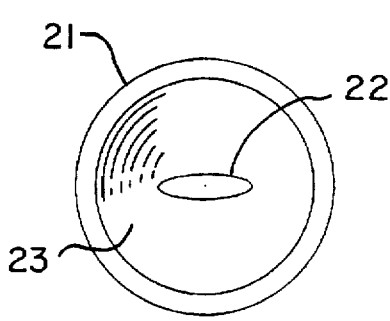
FIG. 1 is a rear elevation view of a transparent artificial eyepiece blank used in carrying out the invention.
Figure 2:
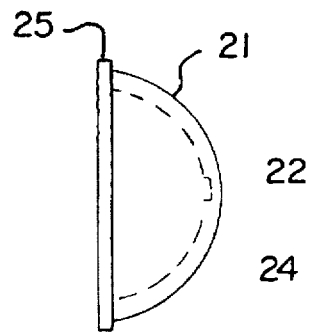
FIG. 2 is a side elevation view of the transparent artificial eyepiece blank of FIG. 1.
Figure 3:
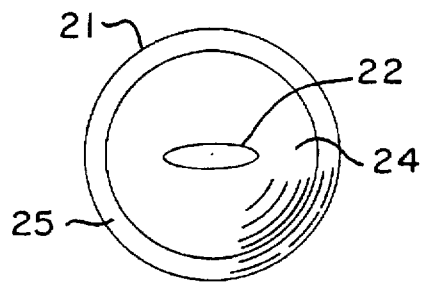
FIG. 3 is a front elevation view of the transparent artificial eyepiece blank of FIG. 1.
Figure 4:
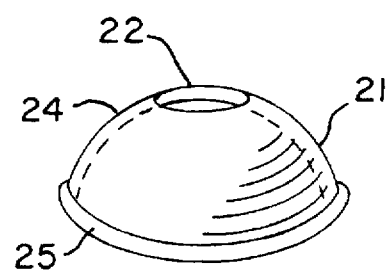
FIG. 4 is a perspective view of the transparent artificial eyepiece blank of FIG. 1.

The present invention will be described with reference to an exemplary procedure for fabricating a realistic artificial deer eye with an integrally formed nictitating membrane. It should be understood, however, that the present invention is applicable to artificial animal eyepieces in general, and may be applied to taxidermy mounts for other animals that have eyes including nictitating membranes.

FIGS. 1, 2, 3 and 4 show an artificial deer eyepiece blank 21. The eyepiece blank 21 is made of transparent glass, and is a semi-spherical shell having its concavity in the rear or inner surface 23 thereof, having a convex outer surface 24, and having a flange 25 extending from the base of the eyepiece 21 around the circumference thereof. A concavity on the concave inner surface 23 of the eyepiece forms an elongated pupil area 22. Such eyepiece blanks are available, for example, from K. L. Glasaugen, Postfach 22, Fichtenweg 7, D-96271, Grubam Forst, Germany (part number 32 (deer eye) or part number 35 (antelope eye)). (Note that the eyepiece 21 may be made of the other transparent materials, such as plastic, in which case the coloration methods described below would be replaced by those appropriate for applying color to transparent plastic.)

An artificial animal eye in accordance with the present invention is colored on the concave inner surface 23 thereof to realistically match the natural colors of, in this case, a deer's eye. Coloration representing the deer's nictitating membrane is applied on the outer surface 24 of the eyepiece 21. An exemplary process for coloring the inner surface 23 of the eyepiece 21, and applying the nictitating membrane to the outer surface 24 of the eyepiece 21 will be described with reference to FIGS. 7–11. It should be understood, however, that other methods and materials than those described may be used to apply the desired coloration to the eyepiece, and that the nictitating membrane may be applied to an artificial eyepiece to which animal eye coloration has already been applied on the inner surface thereof.

Figure 5:
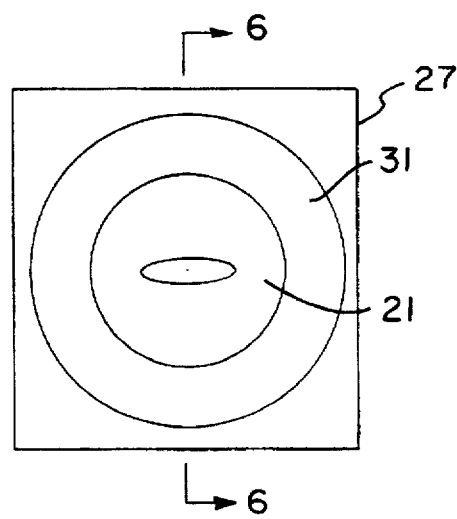
FIG. 5 is a plan view of an artificial eyepiece blank held in an eyepiece template used during the application of coloration to an artificial eyepiece.
Figure 6:
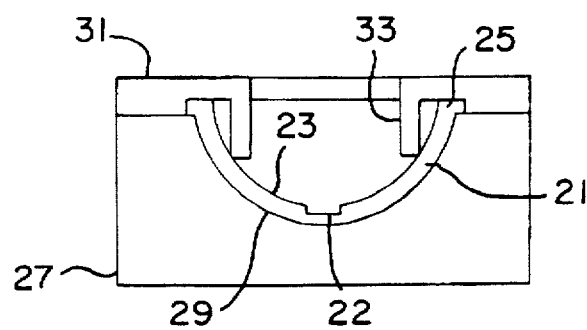
FIG. 6 is a cross-sectional view of the artificial eyepiece and eyepiece template of FIG. 5, taken generally along the line 6—6.

An eyepiece template 27, as illustrated in FIGS. 5 and 6, is preferably used to hold the eyepiece 21 during the application of coloration to the inner concave surface 23 thereof. The template 27 allows coloration to be applied only to selected areas on the concave inner surface 23 of the eyepiece 21. The eyepiece template 27 has a concave well 29 formed therein which corresponds to the shape of the outer convex surface 24 of the artificial eyepiece 21. The artificial eyepiece 21 is placed in the well 29 in the eyepiece template 27 with the flange 25 extending from the base of the artificial eyepiece 21 resting on the top surface of the template 27. A template washer 31 is placed over the artificial eyepiece 21 which is resting in the well 29 of the template 27. The template washer 31 includes a central aperture which is centered over the inner concave surface 23 of the artificial eyepiece 21. A vertical flange or extension 33 from the edge of the central aperture of the washer 31 extends down into the inside of the artificial eyepiece 21, and may contact the concave inner surface 23 of the eyepiece 21. The template washer 31 holds the eyepiece 21 stationary in the template well 29, and forms a template whereby coloration may be applied through the central aperture of the washer 31 onto the concave inner surface 23 of the eyepiece 21, and such that the washer flange 33 keeps the outer circumference of the inner concave surface 23 of the eyepiece 21 free from coloration material that is applied to the central portion of the inner surface 23 of the artificial eyepiece 21. Preferably, the central aperture of the template washer 31 is sized to keep the outer ¼th inch circumference of the inner surface 23 of the eyepiece 21 covered when the washer 31 is in place.

Figure 7:
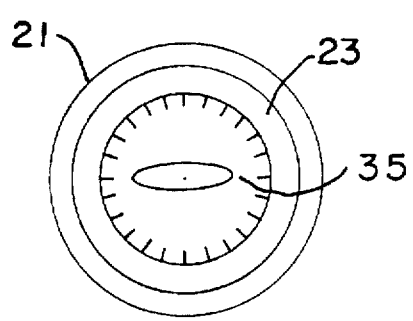
FIG. 7 is a rear elevation view of the artificial eyepiece of FIG. 1 having a texturing coloration glaze applied to a central portion thereof.

Using the eyepiece template 27 to keep the outer circumference of the concave inner surface 23 of the eyepiece 21 covered, a "texturizing material" is applied to a central area 35 of the concave inner surface 23 of the eyepiece 21, as illustrated in FIG. 7. In this case, "texturizing" refers to the application of coloration in a random broken pattern to create a textured appearance. A preferred texturizing coloration material is Cerdec #24-114 black low-fire leaded glass enamel glaze, mixed with distilled water, alcohol, and white shellac. The texturizing coloration material may preferable be applied to the eyepiece 21 using a small piece of natural sea sponge, slightly damped, to dab the texturizing coloration mixture onto the central area 35 of the concave inner surface 23 of the eyepiece 21. This texturizing step provides the artificial eyepiece 21 with the textured appearance found around the pupil area of a deer's eye.

Figure 8:
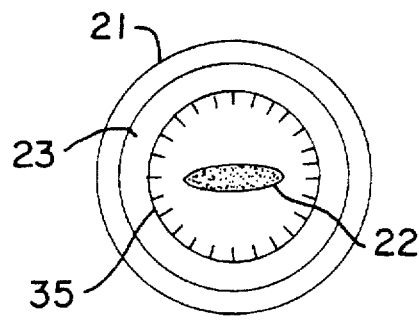
FIG. 8 is a rear elevation view of the artificial eyepiece of FIG. 7 after coloration has been applied to the pupil area thereof.

The pupil area 22 on the inner surface 23 of the artificial eyepiece 21 is preferably colored black, as illustrated in FIG. 8. This coloring of the pupil area 22 is preferably preceded by removing any texturizing glaze applied to the pupil area 22 during the previous texturizing step. Texturizing glaze may be cleaned out of the pupil area 22 using a cotton swab (e.g., a Q-tip). A preferred material for coloring the pupil area 22 is a mixture of Cerdec #24-114 black and #27-4597 blue low-fire leaded glass enamel glazes, alcohol, distilled water, and white shellac. A #0 red sable round brush may be used to flow the pupil coloring glaze into the concave pupil area 22 on the concave inner surface 23 of the eyepiece 21.

The texturizing glaze applied to the central area 35 of the concave inner surface 23 of the eyepiece 21, and the pupil coloring glaze applied to the pupil area 22 of the eyepiece 21 are allowed to dry thoroughly. The artificial eyepiece 21 is then fired in an electric kiln, concave side up, to a temperature of, e.g., 1100° F. Firing causes the glazes to fuse with the eyepiece glass. The fired eyepiece 21 is then allowed to cool completely before proceeding with the application of additional coloration to the eyepiece 21.

Figure 9:
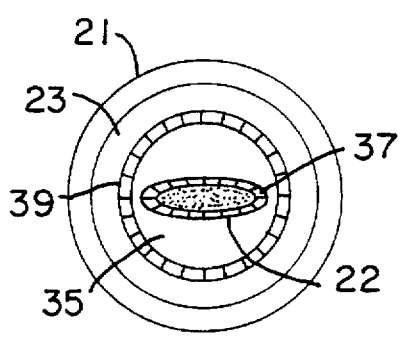
FIG. 9 is a rear elevation view of the artificial eyepiece of FIG. 8 with coloration details applied thereto.

Eye coloration details are preferably applied to the concave inner surface 23 of the artificial eyepiece 21 as illustrated in FIG. 9. Detail areas include a black band 37 around the pupil area 22 of the eyepiece 21, and a circular region 39 between the textured central area 35 of the concave inner surface 23 of the eyepiece 21 and the outer area of the inner concave surface 23 of the eyepiece 21 that was kept clean by using the template 27. The detail coloration may preferably be applied using an air brush, such as the Paasche model VL air brush, to spray a mixture of, e.g., Cerdec #24-114 black low-fire leaded glass enamel glaze, alcohol, distilled water, and white shellac onto the areas 37 and 39.

Figure 10:
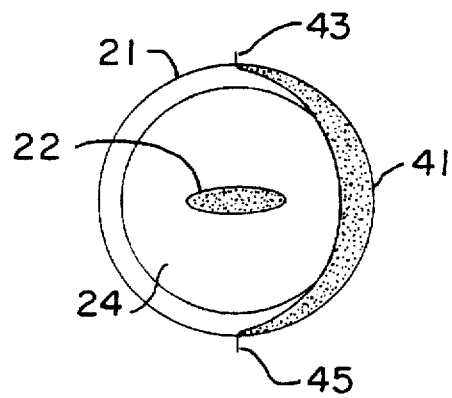
FIG. 10 is a front elevation view of the artificial eyepiece of FIG. 9 with a nictitating membrane formed thereon in accordance with the present invention.

To further enhance the realism of the artificial eyepiece 21, coloration is applied to the convex front surface 24 of the eyepiece 21 to form a nictitating membrane 41, as illustrated in FIG. 10. The nictitating membrane coloration may be formed using a black low-fire leaded glass enamel glaze mixture, including, e.g., Cerdec #24-114 black glaze, alcohol, distilled water, and white shellac. A #2 round red sable brush may preferably be used to apply the nictitating membrane coloration to the convex outer surface 24 of the eyepiece 21 along a portion of the edge thereof in, for an artificial deer eye, the crescent shape of a deer's nictitating membrane. Starting at a top center point 43, aligned with the short (vertical) axis of the pupil area 22, and ending at a bottom center point 45 opposite the starting point, the nictitating membrane coloration is spread along the edge of the convex outer surface 25 of the eyepiece 21 in a crescent shape using the brush. The crescent shaped nictitating membrane 41 is widest at a central point aligned with the long (vertical) axis of the elongated pupil area 22, and is thinnest at its ends 43 and 45. It is preferable that the nictitating membrane 41 at its widest point is not so wide that it completely covers, when viewed from the front of the eyepiece, the space between the outer air-brushed detail area 39 on the inner concave surface 23 of the eyepiece 21 and the outer edge of the inner concave surface 23 of the eyepiece 21. For an artificial deer eye, the widest portion of the nictitating membrane 41 preferably extends approximately ¼ inch from the edge of the eyepiece 21 onto the convex outer surface 24 thereof. Note that the shape of the nictitating membrane 41 illustrated in FIG. 10 corresponds to that of a deer. The size, shape, and position of the nictitating membrane 41 with respect to the pupil area 22 of an eyepiece may be varied as required for the fabrication of artificial animal eyepieces in accordance with the present invention that are to be used for taxidermy mounts of other animals having eyes with nictitating membranes.

The colored glazes applied to the air-brushed detail areas 37 and 39, and forming the nictitating membrane 41, are allowed to dry. The artificial eyepiece 21 is then fired once again, concave side up, to, for example, 1080° F. This firing fuses the nictitating membrane coloration with the eyepiece glass. The nictitating membrane 41 thus becomes an integral part of the eyepiece 21. The eyepiece 21 is then allowed to cool completely.

Figure 11:
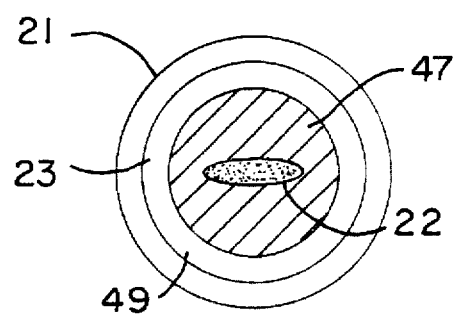
FIG. 11 is a rear elevation view of the artificial eyepiece of FIG. 10 with brown coloration applied to a central portion thereof and a white coloration band formed thereon to complete the artificial eyepiece.

The artificial eyepiece 21 is completed by applying brown and white coloration to the concave inner surface 23 of the eyepiece 21. As illustrated in FIG. 11, for the artificial deer eyepiece 21, brown coloration is applied to a central portion 47 (corresponding to the textured portion 35) of the concave inner surface 23 of the artificial eyepiece 21. The brown coloration may be formed using a mixture of low-fire non-lead glass enamel glazes, e.g., Cerdec #29-801 maroon, #24-8189 black, and #29-8080 burnt orange glazes, mixed with distilled water, alcohol, and shellac. Using the template 27 to keep the outer circumferential area of the inner concave surface 23 of the eyepiece 21 clean, the brown coloration material is applied in an even coat to the central portion 47 of the concave inner surface 23 of the eyepiece 21 using an air brush, such as, e.g., a Paasche model H air brush. Two coats of the brown coloration material are preferably applied to the central area 47 of the concave inner surface 23 of the eyepiece 21, with at least 10 minutes of drying time allowed between the application of each coat.

A band of white coloration 49 is applied on the concave inner surface 23 of the eyepiece 21 in the area of the concave inner surface 23 of the eyepiece 21 located between the brown colored central portion 47 and the outer circumferential edge of the concave inner surface 23 of the eyepiece 21. This area has been kept clean to this point by using the template 27. The white coloration band 49 may be formed using a mixture of low-fire non-leaded glass enamel glazes, e.g., Cerdec #20-8127 white and #23-8074 yellow glazes, mixed with distilled water, alcohol, and white shellac. The white coloration band 49 is formed by removing the eyepiece 21 from the template 27, and spraying the clean circumferential area that was covered by the template washer 31 with an even coat of the white coloration material using, e.g., a Paasche model H airbrush. A second coat of the white coloration material may be applied, after allowing the first coat to dry, if needed. When viewed from the front side of the eyepiece 21, a portion of the white coloration band 49 is preferably visible between the widest portion of the nictitating membrane area 41 and the darker coloration of the central portion 47 of the artificial eyepiece 21.

After the brown and white coloration glazes are allowed to dry thoroughly, the artificial eyepiece is fired in an electric kiln to, e.g., 1060° F., causing the glazes to fuse with the eyepiece glass. The eyepiece 21 is then allowed to cool completely. The completed artificial eyepiece 21, with nictitating membrane 41 integrally formed thereon on the outer convex surface 24 thereof is then ready for use in a taxidermy mount.

Figure 12:
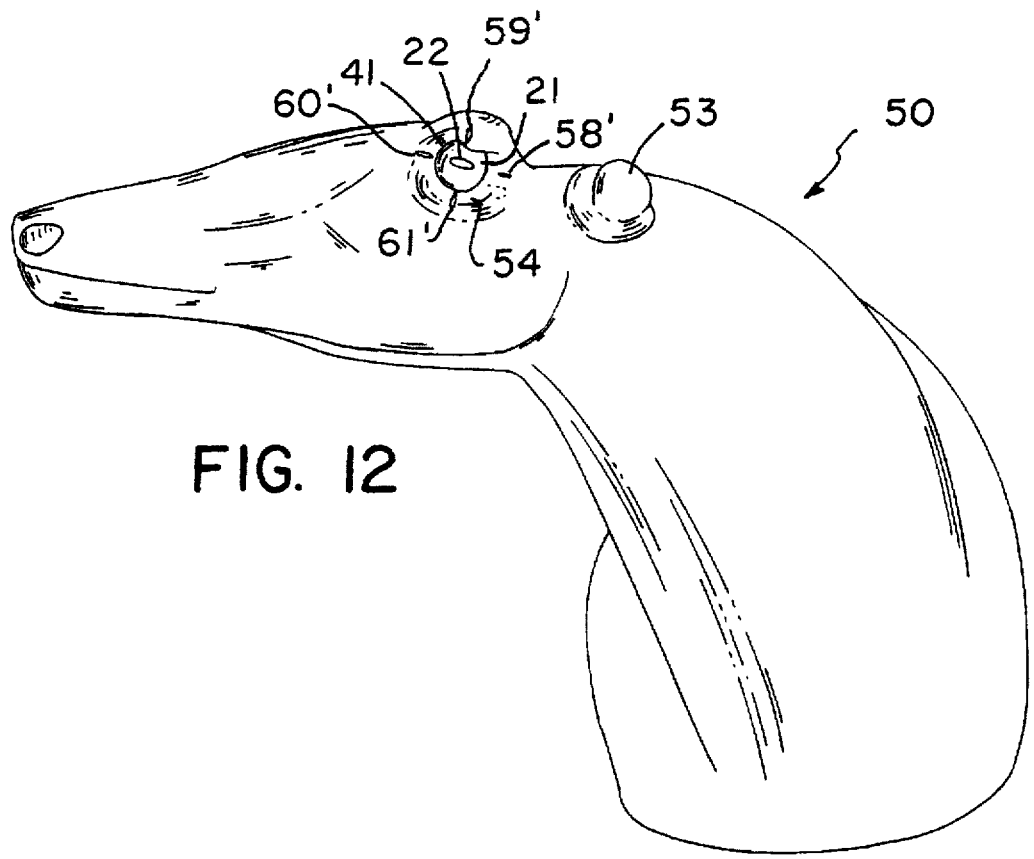
FIG. 12 is a view of a taxidermy mannikin incorporating an artificial eyepiece with integrally formed nictitating membrane in accordance with the present invention.

An artificial animal eyepiece 21 with integrally formed nictitating membrane 41 may be employed in a taxidermy mount by molding the eyepiece 21 into a taxidermy mannikin 50, as illustrated in FIG. 12. The taxidermy mannikin 50 is molded in a conventional manner of lightweight polyurethane foam material, and has, insert-molded therein, the artificial eyepiece 21, which has an elongated pupil 22, and, in accordance with the present invention, a nictitating membrane 41 integrally formed thereon. The mannikin 50 is, in this case, a deer head mannikin having correct deer head anatomical features, including an ear stump indicated at 53 and the eye surrounding features indicated at 54.

Figure 13:
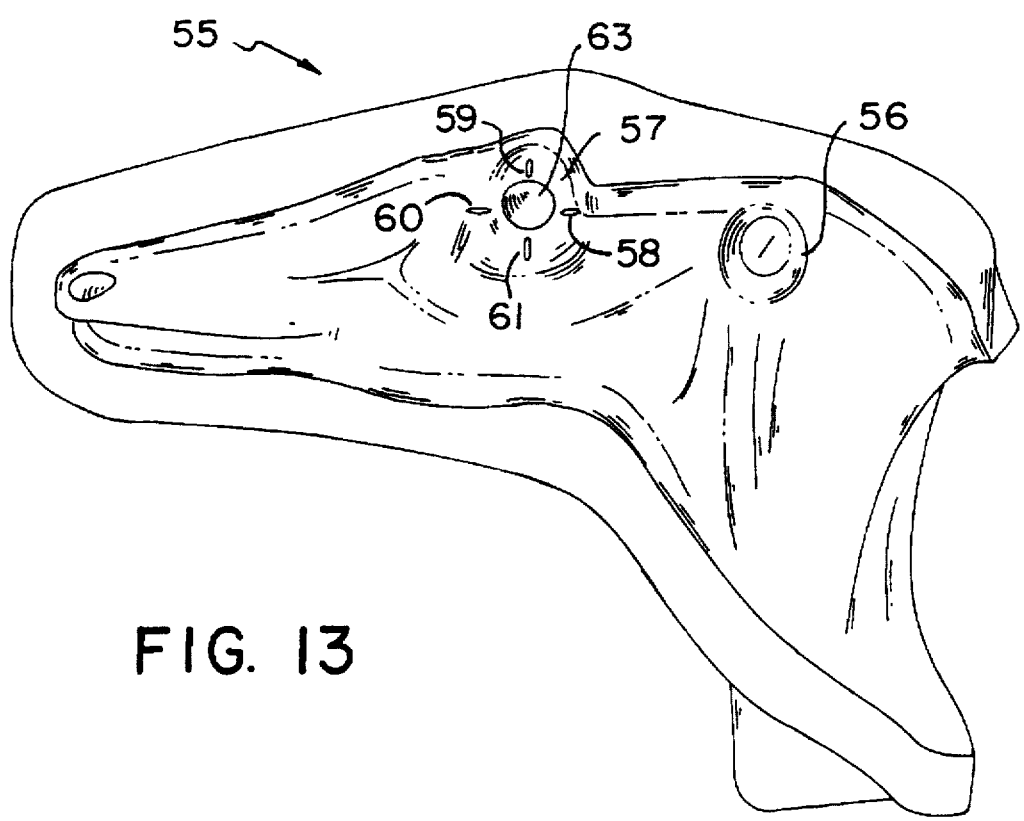
FIG. 13 is a view of the inside of one of the half parts of a mold used to form the taxidermy mannikin of FIG. 12.

In FIG. 13, there is shown the right side half-part 55 of a mold for forming the taxidermy mannikin 50 of FIG. 12. The mold 55 has an ear stump recess 56 in the cavity surface thereof (corresponding to the ear stump 53), and a semi-spherical eye socket recess 63 in which the eyepiece 21 is mounted. The cavity surface of the mold 55 is contoured to correctly form all features of the taxidermy mannikin 50, including the features immediately surrounding the eye and, accordingly, the cavity surface is so contoured as indicated at 57 in FIG. 13 to provide the correct eye surrounding features indicated at 54 in FIG. 1. Ridges 58, 59, 60, and 61 may be formed in the eye socket surrounding area 57 of the mold 55 to serve as indicia markings to facilitate properly positioning the eyepiece 21 in the eye socket recess 63. (These ridges 58, 59, 60, and 61 produce, in the molding process, grooves 58', 59', 60', and 61' on the mannikin 50 as shown in FIG. 1.)

FIG. 14 illustrates how an artificial eyepiece 21 in accordance with the present invention may be placed in proper anatomical orientation in the eye socket recess 63 of the mold 55 by aligning the long axis of the eyepiece pupil area 22 with the ridges 58 and 60 formed in the eye socket surrounding area 57 of the mold 55. The cross sectional view of FIG. 15 illustrates that the eyepiece 21 may be held in the proper anatomical orientation with respect to the alignment ridges 58 and 60 during the subsequent molding process by a removable (cleanable) adhesive 62 which is applied between the inner surface of the mold cavity 55 and the convex outer surface of the eyepiece 21. Note that the rear portion of the eyepiece 21 projects into the cavity of the taxidermy mannikin mold 55.

Two taxidermy mannikin mold half-parts 55, each including an eyepiece 21 in accordance with the present invention secured therein in correct anatomical position in the manner described, are used to form the taxidermy mannikin 50 in a conventional manner. With artificial eyepieces properly positioned and held in each of the mold half-parts, the half-parts are closed together to form a full mold. The taxidermy mannikin 50 is molded by pouring into the mold cavity a liquid polyurethane foaming material, and allowing it to foam expand and harden. The foaming material surrounds the rear portion of the eyepieces 21, and enters the concavities thereof, so as to lock the eyepieces securely in the mannikin 50. When the two half parts of the mold are separated, the resulting mannikin coming out of the mold has the eyes properly positioned in all respects, rotationally and otherwise, and has correct eye-surrounding anatomical features. The taxidermist may then use the taxidermy mannikin to form a realistic mount by mounting an animal skin over the mannikin 50. Further details of forming animal head mannikins with artificial eyepieces fixed therein in correct anatomical orientation using alignment guides in the mannikin mold may be found in U.S. Pat. Nos. 4,432,919, 4,511,522, and 4,515,340, the disclosures of which are incorporated herein by reference.

An alternative method for mounting an artificial eyepiece 21 in accordance with the present invention in correct anatomical orientation in a taxidermy mannikin mold 55 is described with reference to FIGS. 16–19. In this method, an elongated locator piece 70 is affixed to the front portion of the convex outer surface 24 of an artificial animal eyepiece 21 having an integrally formed nictitating membrane 41. The elongated locator piece 70 may be aligned with the pupil area 22 of the eyepiece 21, and should be affixed to the eyepiece 21 with a removable (cleanable) adhesive which will hold the eyepiece 21 in the correct position during the molding operation, and will be removable (cleanable) from the outer surface 24 of the eyepiece 21 after the molding operation. After the locator piece 70 is properly affixed to the outer surface 24 of the eyepiece 21, the eyepiece 21 is inserted into the mold eye socket recess 63 as illustrated in FIGS. 18 and 19. The eyepiece 21 should be inserted into the eye socket recess 63 in such a manner that the elongated locator piece 70 seats within an elongated locator socket 71 that is formed within the eye socket recess 63. When the eyepiece 21 is inserted properly, the elongated pupil 22 will be properly oriented and the eyepiece 21 will be correctly located in relationship with the other features of the mold 55. When inserting the eyepiece 21 into the eye socket recess 63, it is preferable that a cleanable adhesive be place around the locator piece 70 on the outer surface 24 of the eyepiece 21 so that, when the eyepiece 21 is inserted, the cleanable adhesive between the eye socket recess 63 and the outer surface 24 of the eyepiece 21 will hold the eyepiece 21 in position during the molding operation, leaving the rear portion of the eyepiece 21 projecting into the mold cavity. After the molding operation, the cleanable adhesive is removed from the outer surface 24 of the eyepiece 21. It is preferable that the locator piece 70 be resilient and have a lip 77 near the front thereof, and that the locator socket 71 have a corresponding widened portion 78 as shown in FIG. 19. The lip 77 and widened portion 78 together act to retain the locator piece 70 in the locator socket 71 once the eyepiece 21 has been inserted into the socket recess 63. Prior to and during the molding operation, the retention of the locator piece 70 in the locator socket 71 serves to hold the eyepiece 21 in proper anatomical position and rotational orientation. After the polyurethane foam material used to form the mannikin has formed and hardened, and the two half parts of the mold are separated from the formed taxidermy mannikin 50, the lip 77 and widened portion 78 may cause the locator piece 23 to remain within the locator socket 71. Separating the two half parts of the mold from the formed mannikin 50 in such case will serve also to remove the locator piece 70 from the outer surface 24 of the eyepiece 21, since the locator piece 70 was held thereon by a removable (cleanable) adhesive. Further details of forming an animal head mannikin with artificial eyepieces fixed therein in correct anatomical orientation using locator pieces attached to the eyepieces may be found in U.S. Pat. No. 4,753,412, the disclosure of which is incorporated herein by reference.

Methods other than those described may also be used for mounting an artificial animal eyepiece having a nictitating membrane integrally formed thereon into a taxidermy mannikin. Moreover, an artificial eyepiece with integrally formed nictitating membrane in accordance with the present invention may be used for taxidermy mounts which do not employ taxidermy mannikins of the type described in detail herein. Exemplary methods of using an artificial eyepiece with integrally formed nictitating membrane in accordance with the present invention are described herein to illustrate the fact that a realistic taxidermy mount may be more accurately and easily made by employing the artificial animal eyepiece of the present invention. By integrally forming a nictitating membrane on the outer surface of the artificial eyepiece, the act of aligning the eyepiece in a taxidermy mannikin or mannikin mold also automatically positions the nictitating membrane in a correct anatomical position. There is no need for aligning separate eyepiece and nictitating membrane pieces since the nictitating membrane is integrally formed on the eyepiece in the correct anatomical orientation with respect to the other eyepiece features.

It is understood that the invention is not confined to the particular embodiments, materials, and methods of fabrication described herein and illustrated, but embraces such modified forms thereof as come within the scope of the following claims.

What is claimed is:

1. An artificial animal eye for use in taxidermy, comprising:
   (a) a transparent artificial eyepiece blank having a concave inner surface and a convex outer surface;
   (b) animal eye coloration applied on the concave inner surface of the artificial eyepiece blank; and
   (c) an integrally formed nictitating membrane formed of coloration fused to the convex outer surface of the eyepiece blank along an edge thereof.

2. The artificial animal eye of claim 1 wherein the animal eye coloration includes an animal eye texture pattern applied on the concave inner surface of the eyepiece.

3. The artificial animal eye of claim 1 wherein the transparent artificial eyepiece is made of glass and wherein the animal eye coloration includes colored glazes which are applied to the concave inner surface of the artificial eyepiece and fused to the eyepiece.

4. The artificial animal eye of claim 1 wherein the transparent artificial eyepiece is made of glass and wherein the integrally formed nictitating membrane includes a colored glaze applied along the edge of the outer surface of the eyepiece blank and fused to the eyepiece.

5. The artificial animal eye of claim 1 wherein the animal eye coloration on the concave inner surface of the eyepiece includes an elongated pupil section having a long axis and a short axis, and wherein the nictitating membrane is crescent shaped and formed along the edge of the convex outer surface of the eyepiece such that a wide portion of the crescent shaped nictitating membrane is aligned with the long axis of the elongated pupil section and ends of the crescent shaped nictitating membrane are aligned with the short axis of the elongated pupil section.

* * * * *